United States Patent
Itoh

(10) Patent No.: US 8,092,857 B2
(45) Date of Patent: Jan. 10, 2012

(54) THIOPHENE DERIVATIVE AND ORGANIC ELECTROLUMINESCENT ELEMENT

(75) Inventor: Kiyoshi Itoh, Tokyo-to (JP)

(73) Assignee: Dai Nippon Printing Co., Ltd., Tokyo-to (JP)

( * ) Notice: Subject to any disclaimer, the term of this patent is extended or adjusted under 35 U.S.C. 154(b) by 442 days.

(21) Appl. No.: 12/481,869

(22) Filed: Jun. 10, 2009

(65) Prior Publication Data

US 2009/0246902 A1   Oct. 1, 2009

Related U.S. Application Data

(63) Continuation of application No. 11/219,935, filed on Sep. 6, 2005, now abandoned.

(30) Foreign Application Priority Data

Sep. 13, 2004  (JP) ................................. 2004-265935

(51) Int. Cl.
B05D 5/06 (2006.01)

(52) U.S. Cl. ......................................................... 427/64

(58) Field of Classification Search ...................... 427/64
See application file for complete search history.

(56) References Cited

U.S. PATENT DOCUMENTS 5,637,652 A * 6/1997 Kato et al. ..................... 525/389
2007/0173575 A1* 7/2007 Koyama et al. ............... 524/165
* cited by examiner Primary Examiner — Michael Cleveland
Assistant Examiner — Robert Vetere
(74) Attorney, Agent, or Firm — Ladas & Parry LLP

(57) ABSTRACT

The present invention provides a thiophene derivative useful for a material for forming an organic positive hole transport layer of an organic EL element excellent in light emitting efficiency, water resistance or the like, a polymer having the thiophene derivative as a monomer unit, and an organic EL element. The object can be solved by a thiophene derivative represented by the following formula (1), a polymer comprising the thiophene derivative, and an organic EL element, an organic positive hole transporting layer of which comprises the polymer:

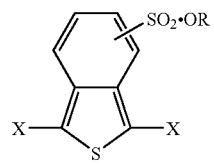

Formula (1)

wherein, each "X" is a halogen atom, which may be same or different from each other; and "R" is an alkyl group.

4 Claims, 1 Drawing Sheet

| Cathode |
|---|
| Electron (injection) transporting layer |
| Light emitting layer |
| Positive hole (injection) transporting layer |
| Anode |

DH type

| Cathode |
|---|
| Electron (injection) transporting layer |
| Positive hole (injection) transporting layer and Light emitting layer |
| Anode |

SH-E type

| Cathode |
|---|
| Electron (injection) transporting layer and Light emitting layer |
| Positive hole (injection) transporting layer |
| Anode |

SH-H type

DH type

SH-E type

SH-H type

THIOPHENE DERIVATIVE AND ORGANIC ELECTROLUMINESCENT ELEMENT

BACKGROUND OF THE INVENTION

1. Field of the Invention

The present invention relates to a thiophene derivative and an organic electroluminescent (hereinafter it is simply referred to as "EL") element. Particularly, it relates to a novel thiophene derivative which is useful for producing an organic electroluminescent element, a polymer thereof, and an organic EL element.

2. Description of the Related Art

An organic EL element comprises a couple of electrodes facing each other and an organic light emitting layer disposed between the couple of electrodes, wherein the organic light emitting layer emits light when an electron injected from one electrode and a positive hole injected from another electrode recombine in the organic light emitting layer. Research and development of such an element fully started when M. Pope, H. P. Kallmann et al. found light emission of a single crystal of anthracene generated by impressing direct voltage in 1963. In 1987, an organic EL element utilizing a laminated structure of organic thin layers was announced for the first time by T. W. Tang, et al. of KODAK.

Thereafter, the organic EL element has been researched and developed aiming for improvement in functions from various aspects such as material, a layer constitution, a method for constituting layers, a method for producing elements or the like. FIG. 1 shows a layer constitution of a general organic EL element. As a material for forming an organic positive hole transporting layer, which has large influence on light emitting property and color property among the layers, polybenzo[c]thiophene sulfonic acid is proposed (Japanese Patent Application Laid-Open (JP-A) No. Sho. 61-17581). Polybenzo[c]thiophene sulfonic acid is a useful conductive polymer material, however, polybenzo[c]thiophene sulfonic acid is basically synthesized by sulfonation of polybenzo[c]thiophene in the presence of sulfuric acid and it is significantly difficult to introduce a sulfonic group to all polybenzo[c]thiophene units. In the case of synthesizing a copolymer of benzo[c]thiophene sulfonic acid and other monomer in order to exhibit various functions, sulfonation is performed after the copolymerizing process, thus, the monomer structure to be copolymerized with polybenzo[c]thiophene may be unnecessarily affected by the sulfonation, which is not efficient.

As aforementioned, various organic materials have been developed to form each layer. Many organic EL elements comprise an organic positive hole transporting layer and an organic light emitting layer as essential layers. Since a material constituting the organic positive hole transporting layer is generally hydrophilic, the material for forming the organic positive hole transporting layer is dissolved or dispersed in water to obtain a coating liquid and the coating liquid is applied on a substrate to form the organic positive hole transporting layer. On a surface of the organic positive hole transporting layer, an organic light emitting layer is formed. Since a material for forming the organic light emitting layer is generally lipophilic, the material for forming the organic light emitting layer is dissolved or dispersed in an organic solvent to obtain a coating liquid and the coating liquid is applied on the organic positive hole transporting layer to form the organic light emitting layer.

Generally, an organic El element is easily affected by moisture, and a performance of element is easily deteriorated by moisture. Hence, in many cases, it has been attempt to eliminate adverse affect of moisture by sealing the organic EL element sufficiently. However, as aforementioned, since the organic positive hole transporting layer is formed with the coating liquid containing water and the material for forming the organic positive hole transporting layer is a hydrophilic material, it is significantly difficult to completely remove even a minute amount of moisture from the organic positive hole transporting layer. In order to moderate adverse influence of the minute amount of remained moisture, efforts such as inclusion of an absorbent in an organic El element upon sealing or the like have been made. However, there are problems that such an effort is cumbersome and requires high production costs.

SUMMARY OF THE INVENTION

Therefore, an object of the present invention is to provide a thiophene derivative which is useful for a material for forming an organic positive hole transport layer of an organic EL element excellent in light emitting efficiency, water resistance or the like, a polymer having the thiophene derivative as a monomer unit, and an organic EL element.

The above object can be attained by the following present invention. That is, the present invention provides a thiophene derivative represented by the following formula (1):

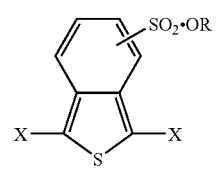

Formula (1)

wherein, each "X" is a halogen atom, which may be same or different from each other; and "R" is an alkyl group.

Also, the present invention provides a polymer represented by the following formula (2), wherein in the case that the polymer is a copolymer, the copolymer is preferably a random copolymer:

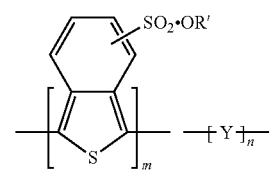

Formula (2)

wherein, "R'" is a hydrogen atom, a counter ion constituting a salt or an alkyl group; "Y" is a divalent aromatic ring; "m" is an integer of 1 or larger; "n" is an integer of 0 or larger; and a repeating unit having a thiophene structure and a repeating unit containing "Y" in a polymer chain may be in any sequence.

Further, the present invention provides an organic EL element comprising at least a pair of electrodes, an organic positive hole transporting layer and an organic light emitting layer disposed between the pair of electrodes, wherein the organic positive hole transporting layer comprises the polymer represented by the formula (2).

A polymer represented by the formula (2) having an alkyl group as "R'" of the present invention is soluble to an organic solvent. Thus, a liquid of the polymer in the organic solvent which contains no water can be applied on a substrate or the like to form an organic positive hole transporting layer. Since the organic positive hole transporting layer thus formed does not contain moisture, moisture may not be included in the organic positive hole transporting layer even if an organic light emitting layer is provided on a surface of the organic positive hole transporting layer. Also, after forming the organic positive hole transporting layer by the polymer represented by the formula (2), the alkyl group referred as "R'" of the formula (2) may be substituted by a hydrogen atom or a counter ion forming a salt and then an organic light emitting layer may be formed thereon. In either manner, an organic EL element in which deterioration of performance due to moisture is significantly inhibited can be provided.

DETAILED DESCRIPTION OF THE INVENTION

Figure 1:
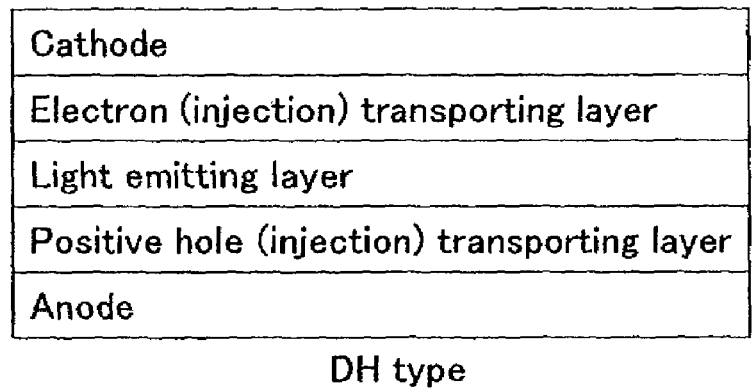
FIG. 1 shows an example of structure of an organic EL element.
Figure 1:
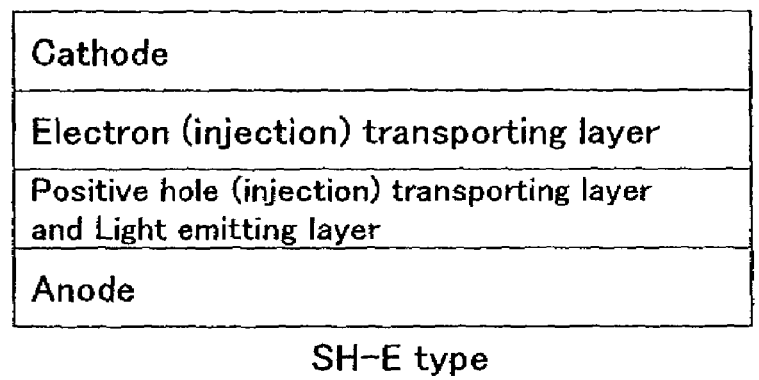
Figure 1:
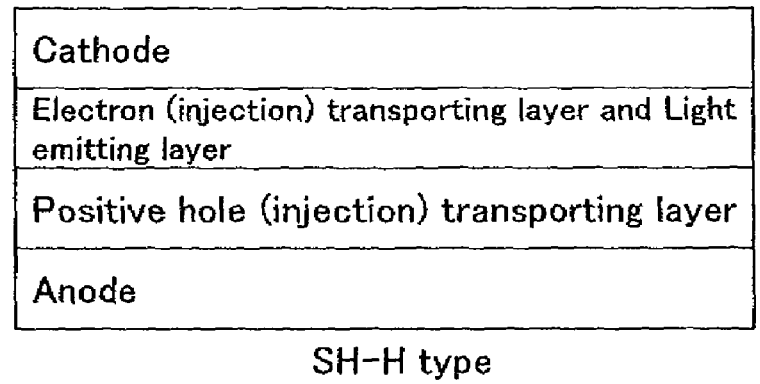

Next, the present invention will be explained in detail with best mode for carrying out the invention. The thiophene derivative represented by the formula (1) may be obtained by a method in which after sulfonating commercially available 2,7-dihalogenobenzo[c]thiophene by a sulfonation agent such as fuming sulfuric acid or the like, the sulfonic group is alkylated by an alkylation agent such as dialkyl sulfate or the like, a method in which after chlorosulphonating 2,7-dihalogenobenzo[c]thiophene, esterification is performed with the use of alkyl alcohol, or the like. As halogen, there may be chlorine, bromine, iodine or the like. Among them, bromine is preferable taking subsequent polymerization into account. As the alkyl group of the alkylation agent, a low to middle molecular weight alkyl group having 1 to 10 carbons is preferable. As alkyl alcohol, there may be low to middle molecular weight alkyl alcohol such as methanol, ethanol, propanol, butanol, pentanol or the like.

The thiophene derivative represented by the formula (1) is useful as a monomer of the polymer represented by the formula (2). Herein, the formula (2) means a polymer comprising a repeating unit having a thiophene structure and a repeating unit containing "Y", wherein the repeating units may be in any sequence. A polymer, "n" of which is 0 in the formula (2), can be obtained by a homopolymerization of the thiophene derivative represented by the formula (1). Also, a polymer, "n" of which is not 0 in the formula (2), can be obtained by a copolymerization of the thiophene derivative represented by the formula (1) and a dihalogenoaromatic compound such as dibromothiophene or the like. It is preferable that the copolymer is a random copolymer.

Homopolymerization of the thiophene derivative represented by the formula (1) and copolymerization of the thiophene derivative and other monomer may be performed by conventional methods, for example, a general substitution reaction, a polycondensation method, a polyaryl synthesis method based on Suzuki coupling or the like. Thus obtained polymer represented by the formula (2) preferably has a weight average molecular weight (measured by GPC, polystyrene standard) of 10,000 to 500,000. Hence, "m+n" in the formula (2) is about 20 to 1,000. If the molecular weight is less than 10,000, a thermal or electric stability of material sufficient to secure a good light emitting property of an organic EL element cannot be obtained. On the other hand, if the molecular weight is more than 500,000, solubility to an organic solvent required to produce an organic EL element may not be obtained.

As other monomer unit in the case that the polymer represented by the formula (2) of the present invention is a copolymer, that is, "Y", there may be aromatic rings such as thiophene, bithiophene, terthiophene, benzo[c]thiophene, dibenzothiophene, biphenyl, naphthalene, anthracene, pyrene, terphenyl, carbazole, triphenylene, chrysene, benzanthracene, bipyridine, terpyridine, pentacene, benzofuran, dibenzofuran, benzimidazole, indene, quinoline, phenanthroline, benzothiazole, fluorene, 9,9-diarylfluorene, 9,9-dialkylfluorene or the like. The total of "m" and "n" of the polymer represented by the formula (2) containing such a monomer unit is as aforementioned and it is preferable that a relationship between "m" and "n" is m≧n.

The polymer represented by the formula (2), "R'" of which is a hydrogen atom or a counter ion forming a salt, can be obtained by eliminating an alkyl group from —$SO_2$.OR' of an ester type in a derivative of the formula (2). A method of elimination may be hydrolysis, heating, irradiation of active radiation or the like. A preferable method is a method in which after forming an organic positive hole transporting layer with a liquid of the polymer having —$SO_2$.OR' of the ester type among the formula (2), an alkyl group is eliminated by heating. Also, after hydrolyzing the polymer having —$SO_2$.OR' of the ester type among the formula (2) by a general method, an organic positive hole transporting layer may be formed with the obtained polymer having a sulfonic group similarly in a conventional manner.

In the present invention, the polymer represented by the formula (2) may be used as it is. Electrical conductivity of the polymer further improves by doping a dopant to the polymer. As the dopant, for example, there may be a halide anion of Vb group element such as $PF_6^-$, $SbF_6^-$, $AsF_6^-$ or the like; a halide anion of IIIb group element such as $BF_6^-$ or the like; a halogen anion such as $I^-$, $Br^-$, $Cl^-$ or the like; perhalogen acid anion such as $ClO_4^-$ or the like; Lewis acid, proton acid, an electrolyte anion, a polymer electrolyte anion or the like. The doped polymer of the present invention is also useful as a conductive polymer material.

Next, a method for producing an organic EL element using the polymer of the present invention will be explained. A substrate to be used in the present invention may be a substrate conventionally used for an organic EL element, generally a glass substrate. For example, a substrate of an organic El element which is a glass substrate having a transparent electrode such as ITO or the like provided on the surface may be used. The substrate may not be particularly limited in the present invention.

In the present invention, firstly, an organic positive hole transporting layer is formed on a surface of the substrate such as a glass substrate or the like directly or via other layers. Herein, the organic positive hole transporting layer of in the present invention means a layer using an organic compound as a material having positive hole transporting property. Specifically, the polymer having —$SO_2$.OR' of the ester type of the present invention is dissolved or dispersed in an organic solvent such as chloroform, methylene chloride, dichloroethane, tetrahydrofuran, toluene, xylene or the like to prepare a coating liquid. Concentration of the polymer in the coating liquid depends on a molecular weight of the polymer or a degree of doping. Generally, the polymer is solved or dispersed in the solvent to be concentration of 0.1 mass % or more, preferably about 1.0 to 5.0 mass %. Thus obtained coating liquid is applied on the substrate and dried, thereby, a layer to be an organic positive hole transporting layer is formed.

Further, by radiating heat energy or radial ray to the thus formed thin layer, the ester bond ($SO_2.OR'$) is decomposed, and an esterificated sulfonic group is modified to a sulfonic group in a free state or a state of salt. To provide the heat energy, for example, a heat treatment at about 200 to 220° C. for about 60 to 90 minutes may be performed. The heat treatment may be simultaneously performed at the time of heat drying after applying the coating liquid. As the radial ray, for example, there may be ultraviolet ray, electron beam or the like. As an irradiation condition of the ultraviolet ray, for example, there may be irradiation of ultraviolet ray of about 200 to 250 mJ/cm$^2$ (wavelength of 300 nm or less). A radiation condition of the electron beam is, for example, 500 KV or more and 35 mA. In such a treatment, the ester bond is decomposed and a desired organic positive hole transporting layer is formed.

The organic positive hole transporting layer does not contain moisture nearly at all since water is not used as medium of the coating liquid of the organic positive hole transporting layer, a water-based material is not used as any other material in the coating liquid, the organic positive hole transporting layer itself is not hydrophilic before eliminating the alkyl group from —$SO_2.OR'$ of the ester type, and water is not used at all in the aforementioned treatment of radiating heat energy or radial ray. Further, a lipophilic (hydrophobic) thin layer (for example, an organic light emitting layer) is formed on a surface of the organic positive hole transporting layer in the next step. Therefore, an organic EL element can be produced under a condition of an inert atmosphere from beginning to end, and the possibility is highly scarce that moisture in the atmosphere is absorbed to the organic positive hole transporting layer during production and after production.

In the present invention, a thin layer comprising a hydrophobic material, for example, an organic light emitting layer required for an organic EL element, is formed on a surface of the thus formed organic positive hole transporting layer. Herein, the organic light emitting layer of the present invention means a layer using an organic compound as a light emitting material. A material for forming the organic light emitting layer may not be particularly limited. For example, there may be naphthalene derivatives, anthracene or derivatives thereof, perylene or derivatives thereof, dyes such as polymethines, xanthenes, coumarins, cyanines or the like, aromatic amine, tetraphenylcyclopentadiene or derivatives thereof, tetraphenylbutadiene or derivatives thereof or the like.

In the present invention, since the organic light emitting layer is formed by the hydrophobic material on the surface of the organic positive hole transporting layer formed as aforementioned, the organic light emitting layer also functions as a vapor barrier of the organic positive hole transporting layer. Hence, the possibility of absorption of moisture in the atmosphere by the organic positive hole transporting layer is highly scarce so that a cumbersome sealing process such as enclosure of an absorbent in an organic EL element as in prior arts can be significantly simplified.

A constitution of the organic EL element in the present invention can be in various embodiments as far as the organic EL element has the above-mentioned constitution. For example, as for a pair of electrodes comprising an anode and a cathode, it is desirable that at least one of the electrodes is transparent or semi-transparent and light emission is performed from the transparent or semi-transparent electrode side in order to obtain an organic EL element having a light emission from a plane face. However, such a requirement is not necessary in the case of emitting light from an end face of the organic EL element.

If the direction of light emission of the organic EL element is at the substrate side, it is desirable that the substrate and an electrode provided on the substrate among the electrodes of the organic EL element are transparent or semi-transparent. For the substrate, a glass plate such as quartz, soda glass or the like, a metal plate or a metal foil, a plastic such as an acrylic resin, a styrene resin, a polycarbonate resin or the like may be used. A thickness of the substrate may be as conventional, and may not be limited.

As the anode, a conductive metal oxide, metal thin layer or the like may be used. Specifically, there may be a conductive metal oxide such as tin oxide, zinc oxide, indium oxide, indium tin oxide (ITO) or the like, a metal such as gold, silver, chromium, nickel or the like, an organic conductive material such as polyaniline, polythiophene, polypyrrole or the like, or a mixture or a laminate thereof. Particularly, ITO may be preferably used as an anode from the viewpoint of high conductivity, transparency and the like. A method for forming the anode may be a conventional method, and may not be limited. Also, a thickness of the anode may be as conventional, and may not be limited.

As a method for forming the organic positive hole transporting layer and the organic light emitting layer, it is particularly preferable to form a layer by a coating or printing method such as a spin coating method, a cast coating method, a dip coating method, a die coating method, a bead coating method, a bar coating method, a roll coating method, a spray coating method, a gravure coating method, a flexographic printing method, a screen printing method, an off set printing method or the like using the aforementioned organic solvent type liquid or dispersion, or a mixture thereof.

A thickness of the organic positive hole transporting layer may be 1 nm to 1 μm, preferably 2 nm to 500 nm, more preferably 5 nm to 200 nm. A thickness of the organic light emitting layer may be 1 nm to 1 μm, preferably 2 nm to 500 nm, more preferably 5 nm to 200 nm. In the case of forming the layer by the coating method, heat drying may be preferably performed under a condition of low pressure or inert atmosphere at 30 to 300° C., preferably 60 to 200° C., in order to remove the solvent. In such a case of laminating the organic light emitting layer and the organic positive hole transporting layer, the organic positive hole transporting layer is formed on the anode before providing the organic light emitting layer by the above mentioned method for forming a layer.

Next, a cathode is provided on the organic light emitting layer or via other layer. As a material for the cathode, a material having a work function of 4 eV or less may be preferable so that an electron can be easily injected. There may be an alkali metal such as lithium, sodium, cesium or the like, halide thereof such as lithium fluoride, sodium fluoride, cesium fluoride, lithium chloride, sodium chloride, cesium chloride or the like, an alkaline-earth metal such as calcium, magnesium or the like, halide thereof such as calcium fluoride, magnesium fluoride, calcium chloride, magnesium chloride or the like, a metal such as aluminum, silver or the like, a conductive metal oxide thereof, an alloy thereof, a mixture thereof or the like.

As a method for forming the cathode, a vapor deposition method, a spattering method, a laminating method, in which a metal thin layer is compressed, or the like may be used. After forming the cathode, it is desirable to provide a protective layer or a protective cover to protect an organic EL element from outside in order to use the organic EL element stably for a long period. As the protective layer, there may be used a polymer compound, metal oxide, metal fluoride, metal boride, silicon oxide, silicon nitride or the like. As the protective cover, a glass plate, a plastic plate having a low hydraulic permeability treatment on the surface or the like may be used. In one of the preferable method, the protective cover is bonded to the substrate of the organic EL element with a heat-curable resin or a photocurable resin to seal the organic EL element.

In order to obtain a plane-shaped light emitting element using the organic EL element of the present invention, plane-shaped anode and cathode may be disposed to be overlaid. Also, as a method to obtain a pattern-formed light emission, there may be a method to dispose a mask having a pattern-formed window on the surface of the plane-shaped light emitting element, a method in which an organic layer of a non-light emitting portion is formed to have a quite large thickness so as to be substantially non-light emitting, or a method of forming the anode and/or the cathode in a pattern form.

Further, as a method to form a dot matrix element, there may be a method to form an anode and a cathode in a striped form and arrange the anode and the cathode in perpendicular state, a method to enable one electrode to be selectively driven by TFT, or the like. Also, by arranging multiple organic EL elements having different light emitting colors on the same surface, partial color display, multiple color display and full-color display are possible.

EXAMPLES

Next, the present invention will be explained further in detail with reference to the examples. The present invention may not be limited to the examples. "Part(s)" mentioned hereinafter is based on mass if not particularly mentioned.

Example 1

5.27 parts of dibromo-o-toluene was heated to reflux in 70 parts of toluene in the presence of phosphorus trisulfide for 8 hours to obtain benzo[c]thiophene. 0.86 parts of thus obtained benzo[c]thiophene was heated to reflux with 0.56 parts of cuprous bromide in dehydrated methylene chloride for 5 hours to obtain 0.47 parts of dibromobenzothiophene. The bromide was sulfonated by fuming sulfuric acid. The sulfide was heated to reflux with an excessive amount of dibutyl sulfate in dehydrated tetrahydrofuran for 12 hours. Then, an unreacted product and impurity were removed, dried under reduced pressure, and thus obtained a thiophene derivative of the present invention represented by the formula 1a (brown powder, decomposition temperature: 157° C. (elimination of a dibutyl group), melting point: 270° C.):

Formula 1a:

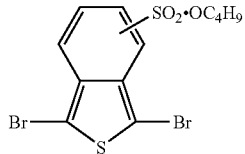

The results of elementary analysis and NMR analysis of the compound represented by the formula 1a are as follows.
[Elementary Analysis]
  Calculated value C=33.7, H=2.8, S=15.0, O=11.2
  Analyzed value C=33.5, H=2.9, S=14.8, O=10.9
[NMR Data]

$^1$H-NMR (CDCl$_3$) δ: 1.22 (t, 3H), 1.81 (m, 2H), 2.43 (m, 2H), 4.47 (q, 2H), 7.33 to 7.80 (m, 3H)
$^{13}$C-NMR (CDCl$_3$) δ: 13.8, 19.2, 35.6, 61.8, 112.2, 122.4, 125.3, 127.0, 134.2

Examples 2 to 4

In Example 2, in the same manner as in Example 1 except that dimethyl sulfate was used instead of dibutyl sulfate, a thiophene derivative 1b of the present invention in which the butyl group represented by the formula 1a was a methyl group was obtained.

In Example 3, in the same manner as in Example 1 except that diethyl sulfate was used instead of dibutyl sulfate, a thiophene derivative 1c of the present invention in which the butyl group represented by the formula 1a was an ethyl group was obtained.

In Example 4, in the same manner as in Example 1 except that dipropyl sulfate was used instead of dibutyl sulfate, a thiophene derivative 1d of the present invention in which the butyl group represented by the formula 1a was a propyl group was obtained.

The analysis results are shown in Table 1.

TABLE 1

| Compound | | Estere limination temperature (° C.) | Melting point (° C.) | Elementary analysis (measured value) | | | |
|---|---|---|---|---|---|---|---|
| | | | | C | H | S | O |
| Example 2 | 1b | 149-151 | 255 | 27.8 | 1.4 | 16.5 | 11.9 |
| Example 3 | 1c | 153 | 250 | 31.1 | 2.3 | 16.2 | 12.2 |
| Example 4 | 1d | 178 | 290 | 31.9 | 2.5 | 15.3 | 12.1 |

Example 5

4.3 parts of the thiophene derivative represented by the formula 1a obtained in Example 1 and 2.4 parts of 2,5-dibromothiophene were heated to reflux in dimethyl formamide in the presence of nickel chloride and triphenyl sulfone for 4 hours, thus obtained 0.7 parts of a copolymer represented by the following formula 2a, wherein a weight average molecular weight (measured by GPC, polystyrene standard) of the obtained copolymer obtained was 20,000 and the copolymer was soluble to toluene by 1 mass % or more:

Formula 2a:

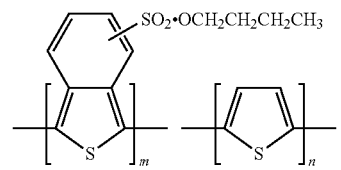

Example 6

In the same manner as in Example 5 except that an equimolar 2,7-dibromofluorene was used instead of 2,5-dibromothiophene, a copolymer represented by the following formula 2b was obtained, wherein a weight average molecular weight (measured by GPC, polystyrene standard) of the copolymer obtained was 15,000 and the copolymer was soluble to toluene by 1 mass % or more:

Formula 2b:

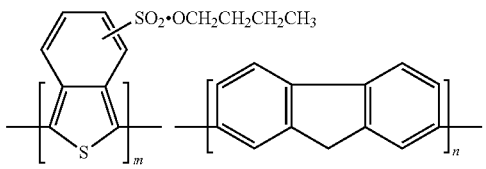

Example 7

In the same manner as in Example 5 except that an equimolar thiophene derivatives 1b, 1c and 1d were respectively used instead of thiophene derivative 1a, copolymers represented by the following formulae 2c, 2d and 2e respectively were obtained, wherein weight average molecular weight (measured by GPC, polystyrene standard) of each copolymers obtained was 15,000 to 25,000 and each copolymer was soluble to toluene by 1 mass % or more:
Formulae 2c to 2e:

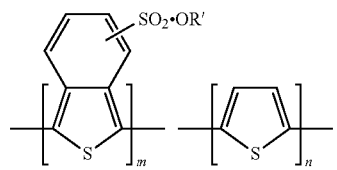

wherein, "R'" is a methyl group for the copolymer 2c, an ethyl group for the copolymer 2d and a propyl group for the copolymer 2e.

Example 8

After washing and UV/ozonation of a glass substrate having an ITO transparent conductive layer formed, a 1 mass % toluene liquid of the copolymer 2a of Example 5 was spin coated on the glass substrate followed by drying in a room temperature for 30 minutes and drying by heat on a hot plate at 160° C. for 1 hour, thereby, an organic positive hole transporting layer having a thickness of 60 nm comprising a copolymer having a butyl group eliminated from a sulfobutoxy group of the copolymer 2a. Next, a red ink for a light emitting layer (product name: ADS100TS; manufactured by American Dye source, Inc.) was spin coated dropwise on the organic positive hole transporting layer similarly followed by drying by heat on a hot plate at 100° C., thus obtained a red organic light emitting layer having a thickness of 80 nm. After forming the red light emitting layer, a calcium thin layer having a thickness of 10 nm was vapor deposited at a speed of 0.2 nm/s, and a silver thin layer was further vapor deposited thereon at the speed of 0.2 nm/s to form an electrode, thus obtained an organic EL element. The ITO electrode of the organic EL element obtained was connected to a positive electrode of a variable direct-current power supply and the electrode of the silver thin layer was connected to a negative electrode of the variable direct-current power supply. When direct voltage was impressed, a good red EL light emission having a maximum light emitting efficiency of 0.5 cd/A was obtained from the light emitting layer.

In the same manner as in Example 8 except that the copolymers 2b, 2c, 2d and 2e were respectively used instead of the copolymer 2a, organic EL elements having excellent red light emitting efficiency were obtained respectively.

According to the present invention, a thiophene derivative which is useful as a material for forming an organic positive hole transporting layer of an organic EL element excellent in light emitting efficiency, water resistance or the like, a polymer comprising the thiophene derivative as a monomer unit, and an organic EL element, an organic positive hole transporting layer of which comprises the polymer, can be provided.

What is claimed is:

1. A method of producing an organic electroluminescent element comprising at least a pair of electrodes, an organic positive hole transporting layer and an organic light emitting layer disposed between the pair of electrodes, which method comprising the steps of:
   preparing a coating liquid by dissolving at least a polymer represented by the following formula (2) in an organic solvent; and
   forming the organic positive hole transporting layer by applying the coating liquid on one of the electrodes, drying the same, and eliminating an alkyl group from a sulfonate ester in the polymer represented by the following formula (2) to form a sulfonic acid:

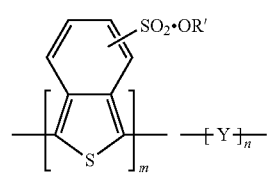

Formula (2)

wherein "R'" is an alkyl group; "Y" is a divalent aromatic ring; "m" is an integer of 1 or larger; and "n" is an integer of 0 or larger.

2. The method of producing an organic electroluminescent element according to claim 1, wherein, in the polymer represented by Formula (2), "n" is an integer of 1 or larger; and the divalent aromatic ring "Y" is at least one selected from the group consisting of thiophene, bithiophene, terthiophene, benzo[c]thiophene, dibenzothiophene, biphenyl, naphthalene, anthracene, pyrene, terphenyl, carbazole, triphenylene, chrysene, benzanthracene, bipyridine, terpyridine, pentacene, benzofuran, dibenzofuran, benzimidazole, indene, quinoline, phenanthroline, benzothiazole, fluorene, 9,9-diarylfluorene and 9,9-dialkylfluorene.

3. The method of producing an organic electroluminescent element according to claim 1, wherein, in the step of forming the organic positive hole transporting layer, an alkyl group is eliminated from a sulfonate ester to form a sulfonic acid by irradiation with heat energy or radial ray.

4. The method of producing an organic electroluminescent element according to claim 1, wherein "R'" in Formula (2) is an alkyl group having 1-10 carbon numbers.

* * * * *